United States Patent
O Neill et al.

(10) Patent No.: US 9,182,361 B2
(45) Date of Patent: Nov. 10, 2015

(54) DIGITAL X-RAY IMAGING SYSTEM WITH STILL AND VIDEO CAPTURE MODES

(71) Applicant: Ann Arbor Digital Devices Inc., Chelsea, MI (US)

(72) Inventors: William J. O Neill, Ann Arbor, MI (US); Brian T. O Neill, Ann Arbor, MI (US); David C. Blake, Ann Arbor, MI (US)

(73) Assignee: Ann Arbor Digital Devices Inc., Dexter, MI (US)

( * ) Notice: Subject to any disclaimer, the term of this patent is extended or adjusted under 35 U.S.C. 154(b) by 97 days.

(21) Appl. No.: 14/249,017

(22) Filed: Apr. 9, 2014

(65) Prior Publication Data
US 2014/0355738 A1    Dec. 4, 2014

Related U.S. Application Data

(60) Provisional application No. 61/855,922, filed on May 28, 2013.

(51) Int. Cl.
*H05G 1/58*    (2006.01)
*G01N 23/04*    (2006.01)
*B60P 1/43*    (2006.01)
(Continued)

(52) U.S. Cl.
CPC    *G01N 23/04* (2013.01); *A61B 6/02* (2013.01); *A61B 6/4225* (2013.01);
(Continued)

(58) Field of Classification Search
CPC ..... G01N 23/04; G01N 23/08; G01N 23/083; A61B 6/44; A61B 6/4417; A61B 6/4429; A61B 6/46; A61B 6/465; A61B 6/467; A61B 6/4233; A61B 6/00; G01T 1/2928; G01T 1/2018

USPC ........... 378/62, 98, 98.2, 98.8, 114, 115, 116, 378/167
See application file for complete search history.

(56) References Cited

U.S. PATENT DOCUMENTS

2006/0027759 A1    2/2006    Jiang et al.
2006/0188064 A1    8/2006    Razzano et al.
(Continued)

FOREIGN PATENT DOCUMENTS

DE    102008049048 A1    6/2010
WO    WO9614593 A1    5/1996

OTHER PUBLICATIONS

Authorized Officer Tae Hoon Kim, Notification of Transmittal of the International Search Report and the Written Opinion of the International Searching Authority, International Application No. PCT/US2014/039618, mailed Sep. 24, 2014, 11 pages.

*Primary Examiner* — Jurie Yun
(74) *Attorney, Agent, or Firm* — Fish & Richardson P.C.

(57) ABSTRACT

In one aspect, a system includes a conventional, film-based X-ray machine and a digital imaging assembly. The X-ray machine includes an X-ray source and a bracket assembly configured to hold X-ray film. The digital imaging assembly is configured to be mounted on the bracket assembly of the X-ray machine. The digital imaging assembly includes a scintillation screen and a digital image sensor. The digital image sensor is coupled with one or more processors that is configured to receive user input that selects a mode of operation from between a still image capture mode and a video capture mode, receive digital signals from the digital image sensor, process the digital signals to generate digital X-ray image data in accordance with the selected mode of operation, and present the generated digital X-ray image data on a display device.

20 Claims, 3 Drawing Sheets

(51) Int. Cl.
  *A61B 6/02* (2006.01)
  *A61B 6/00* (2006.01)
  *G03B 42/02* (2006.01)
  *G03B 42/04* (2006.01)
(52) U.S. Cl.
  CPC .............. *A61B 6/4233* (2013.01); *A61B 6/486* (2013.01); *B60P 1/431* (2013.01); *G03B 42/021* (2013.01); *G03B 42/04* (2013.01); *Y10T 29/49826* (2015.01)

(56) References Cited

U.S. PATENT DOCUMENTS

| | | |
|---|---|---|
| 2008/0112535 A1 | 5/2008 | Wojcik et al. |
| 2008/0290280 A1 | 11/2008 | Ruetten et al. |
| 2009/0181491 A1 | 7/2009 | Roizin et al. |
| 2011/0163236 A1 | 7/2011 | Arodzero |
| 2011/0206181 A1 | 8/2011 | Linev |
| 2013/0126753 A1 | 5/2013 | Aylward et al. |
| 2013/0208857 A1 | 8/2013 | Arodzero et al. |

DIGITAL X-RAY IMAGING SYSTEM WITH STILL AND VIDEO CAPTURE MODES

CROSS REFERENCE TO RELATED APPLICATION

This disclosure claims the benefit of priority under 35 U.S.C. §119(e) of U.S. Provisional Application No. 61/855,922, filed May 28, 2013, the disclosure of which is hereby incorporated by reference in its entirety.

BACKGROUND

This specification relates to an X-ray imaging system.

Conventional diagnostic X-ray machines capture static X-ray images of an object on X-ray film. An X-ray source is used to generate X-rays that illuminate the X-ray film plane upon which the object is positioned at a known distance from the X-ray source. The X-ray generator exposes the object and the X-ray film. After exposure, the X-ray film is treated in a series of chemical baths to produce an X-ray image of the object. A light box is typically used to view the X-ray image.

SUMMARY

This specification describes technologies relating to a digital X-ray imaging system with still and video capture modes. In general, one innovative aspect of the subject matter described in this specification can be implemented in a digital X-ray imaging system that may include a conventional, film based X-ray machine, a digital imaging assembly, and one or more processors. The conventional, film-based X-ray machine can include an X-ray source that emits X-rays and a bracket assembly configured to hold X-ray film. The digital imaging assembly may be configured to be mounted on the bracket assembly of the conventional, film-based X-ray machine. The bracket assembly may or may not include a pivot plate that allows mounting means such that images can be positioned in the vertical direction or in the horizontal direction. The digital imaging assembly can include a scintillation screen that converts X-ray photons into visible light photons and an image sensor that converts the visible light photons into digital signals. The one or more processors may be coupled with the image sensor and may be configured to receive user input that selects a mode of operation from between a still image capture mode and a video capture mode, receive the digital signals from the digital image sensor, process the digital signals to generate digital X-ray image data in accordance with the selected mode of operation, and present the generated digital X-ray image data on a display device These and other implementations can optionally include one or more of the following features. The digital imaging assembly can include a lens that focuses the visible light photons from the scintillation screen onto the image sensor. The one or more processors can be configured to perform an operation to generate a digital still X-ray image when the selected mode of operation is the still image capture mode. The one or more processors can be configured to perform an operation to generate the digital still X-ray image with an image resolution in a range of 5000×3000 pixels to 6000×4000 pixels. The one or more processors can be configured to perform an operation to generate a continuous series of digital still X-ray images when the selected mode of operation is the video capture mode. The one or more processors can be configured to perform an operation to generate the continuous series of digital still X-ray images with a frame rate in a range of 24 frames per second to 30 frames per second. The one or more processors can be configured to perform an operation to generate the continuous series of digital still X-ray images with a duration in a range of 1 second to 2 seconds. The one or more processors can be configured to perform an operation to generate the continuous series of digital still X-ray images with each of the digital still X-ray images having an image resolution in a range of 800×600 pixels to 1920×1080 pixels. The one or more processors can be configured to receive a first set of digital signals that are generated by the image sensor before the X-ray source starts emitting the X-rays, receive a second set of digital signals that are generated by the image sensor while the X-ray source is emitting the X-rays, and receive a third set of digital signals that are generated by the image sensor after the X-ray source stops emitting the X-rays. The one or more processors can be configured to generate a first set of digital X-ray image data from the first set of digital signals, a second set of digital X-ray image data from the second set of digital signals, and a third set of digital X-ray image data from the third set of digital signals, generate the continuous series of digital still X-ray images from the first set of digital X-ray image data, the second set of digital X-ray image data, and the third set of digital X-ray image data, determine that the first set of digital X-ray image data and the third set of digital X-ray image data includes only blank images, and remove the first set of digital X-ray image data and the third set of digital X-ray image data from the continuous series of digital still X-ray images. The one or more processors can be configured to perform an operation to present the generated digital X-ray image data on the display device within approximately 10 seconds of receiving the digital signals from the digital image sensor. The one or more processors can be configured to perform an operation to receive user input to slow playback speed, adjust brightness, adjust contrast, zoom, grab, measure, or manipulate the digital X-ray image data. The image sensor can comprise at least one of a charge-coupled device (CCD) imaging array or a complementary metal-oxide-semiconductor (CMOS) imaging array. The conventional, film-based X-ray machine can include a controller that causes the X-ray source to emit the X-rays in response to user input received by the controller. The one or more processors can be coupled with the controller of the conventional, film-based X-ray machine, and can be configured to perform an operation to transmit a signal to the controller to cause the X-ray source to emit the X-rays.

Particular implementations of the subject matter described in this specification may be implemented to realize one or more of the following potential advantages. A conventional, film-based X-ray machine can be retrofitted with a digital imaging assembly and a digital image processing system to capture both digital still X-ray images and digital videos of a series of X-ray images. A user can select the mode of capture by, for example, pressing a button, instead of physically removing and replacing one capture device with another capture device. In still image capture mode, the digital X-ray imaging system can capture high resolution still X-ray images. In video capture mode, the digital X-ray imaging system can capture high resolution digital video of moving joints and organs within a body. The processing system can edit and display the captured video within approximately 10 seconds.

Details of one or more implementations of the subject matter described in this specification are set forth in the accompanying drawings and description below. Other features, aspects, and potential advantages of the subject matter will become apparent from the description, the drawings, and the claims.

DETAILED DESCRIPTION

Figure 1:
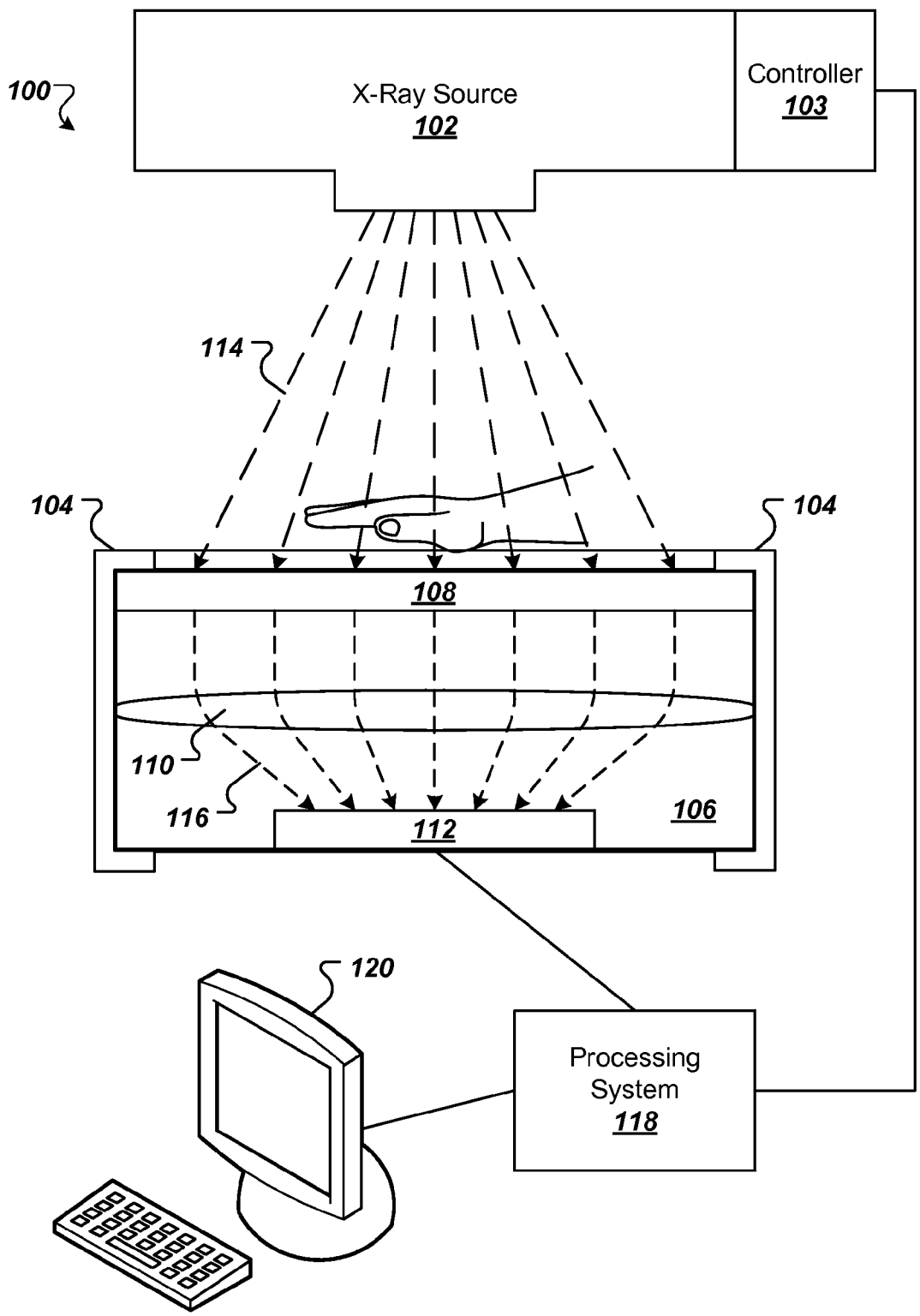
FIG. 1 is a block diagram of an example of a digital X-ray imaging system.

FIG. 1 is a block diagram of an example of a digital X-ray imaging system 100 for generating X-ray images of an object. The digital X-ray imaging system 100 includes an X-ray source 102, a controller 103, and a bracket assembly 104. The X-ray source 102 emits X-rays. The controller 103 causes the X-ray source 102 to emit the X-rays in response to user input received by the controller 103. The bracket assembly 104 may be configured to hold X-ray film or an imaging plate.

The X-ray source 102, the controller 103, and the bracket assembly 104 may be components of a conventional X-ray machine. For example, the conventional X-ray machine may be a conventional, film-based X-ray machine that uses X-ray film to capture a still X-ray image. The X-ray film is treated in a series of chemical baths to produce an X-ray image of the object. A light box is typically used to view the X-ray image.

As another example, the conventional X-ray machine may be a computed radiography (CR) device that is capable of capturing high quality X-ray images. A CR device typically produces one still X-ray image at a time. A CR device is a two phase device whereby an image is first stored on an imaging plate during the exposure phase, and the image stored on the imaging plate is later read and digitized under the processing phase. Following the reading and digitization process, the imaging plate is erased and can be re-used.

A significant amount of time may be required to produce a viewable still X-ray image using conventional X-ray film or a conventional CR imaging plate. To capture and present both digital still X-ray images and digital videos of X-ray images without a significant delay, a digital imaging assembly 106 and a processing system 118 are included in the digital X-ray imaging system 100. The digital imaging assembly 106 converts X-ray energy into visible light energy and visible light energy into digital signals. The processing system 118 processes the digital signals to generate digital X-ray image data and presents the generated digital X-ray image data on a display device 120.

The digital imaging assembly 106 includes a scintillation screen 108, a light collection system 110, and a digital image sensor 112. The scintillation screen 108, the light collection system 110, and the digital image sensor 112 may be enclosed in a light tight enclosure. In some implementations, the digital imaging assembly 106 may be configured to be mounted on the bracket assembly 104. In some implementations, the bracket assembly 104 may be removed and the digital X-ray imaging system 100 may be installed to replace the bracket assembly 104.

The scintillation screen 108 converts X-ray photons 114 into visible light photons 116. The scintillation screen 108 may be a high gain, high resolution scintillation screen. The light collection system 110 may be, for example, a lens that directs or focuses the visible light photons 116 from the scintillation screen 108 onto the image sensor 112. The digital image sensor 112 converts the visible light photons 116 into digital signals. The digital image sensor 112 may include a charge-coupled device (CCD) imaging array or a complementary metal-oxide-semiconductor (CMOS) imaging array.

The processing system 118 is coupled with the digital image sensor 112 for bi-directional communication with the digital image sensor 112. The processing system 118 receives the digital signals from the digital image sensor 112, processes the digital signals to generate digital X-ray image data, and presents the generated digital X-ray image data on the display device 120. The processing system 118 may present a digital still X-ray image on the display device 120 within seconds of receiving the digital signals from the digital image sensor 112. The processing system 118 may present a continuous series of digital still X-ray images, e.g., a digital video of X-ray images, within approximately 10 seconds of receiving the digital signals representing the digital video of X-ray images from the image sensor 112.

The digital X-ray imaging system 100 supports two operating modes that include a still image capture mode and a video capture mode. The digital X-ray imaging system 100 may default, for example, at start-up of the system 100, to the still image capture mode. In the still image capture mode, the digital X-ray imaging system 100 generates digital still X-ray images. In the video capture mode, the digital X-ray imaging system 100 generates digital videos that include a continuous series of digital still X-ray images. To enable a user to select between the two operating modes, the processing system 118 may present a user interface on the display device 120. The user interface may include one or more buttons that, when selected by a user using an input device, switches the digital X-ray imaging system 100 from one operating mode to the other operating mode.

To enable a user to initiate a digital still X-ray image or a digital video capture, the processing system 118 may display a button on the user interface that the user can select to capture a digital still X-ray image or a digital video of X-ray images. When the user selects the button to initiate a capture, the processing system 118 sends a signal to the image sensor 112 to cause the image sensor 112 to acquire image data.

In some implementations, the image sensor 112 may acquire the image data for a predetermined period of time, e.g., 10 to 15 seconds. During the predetermined period of time, the user may take an X-ray by, for example, pressing a button on the controller 103 of the X-ray machine to cause the X-ray source 102 to illuminate an object with X-rays.

In some implementations, the processing system 118 may be coupled with the controller 103 of the X-ray machine. After the user selects the button on the user interface to initiate a capture, the processing system 118 may transmit a signal to the controller 103 to cause the X-ray source 102 to emit the X-rays.

To generate a digital still X-ray image, visible light is integrated upon the image sensor 112 until an exposure is terminated. An exposure can last for up to 0.25 seconds or longer while the X-ray photons 114 are converted to visible light photons 116 by the scintillation screen 108. During the exposure time, digital image data representing a digital still X-ray image is formed upon the imaging sensor 112. The imaging sensor 112 has sufficient spatial resolution to produce diagnostic quality still X-ray images. For example, the digital image sensor 112 can capture digital still images with a resolution of up to approximately 6000×4000 pixels.

In the video capture mode, the digital X-ray imaging system 100 can capture a digital video of real time events over a small period of time in a series of high resolution images, e.g., images with a resolution greater than 640×480 pixels and up to approximately 1920×1080 pixels, at a frame rate of approximately 30 frames per second. For example, the digital X-ray imaging system 100 can capture a dynamic sequence of high resolution images with a time duration of approximately 1 or 2 seconds to record the total range of motion of joints, such as joints of the spine, neck, shoulder, knee, wrist, or elbow. An X-ray beam generated by the X-ray source 102 radiates a moving body part, e.g., a cervical spine moving from extension to flexion, positioned adjacent to the scintillation screen 108, and a sequence of X-ray images is captured by the image sensor 112. A user, such as a physician, can view the sequence of images on the display device 120 to observe paradoxical motion of the joints.

The digital X-ray imaging system 100 may acquire a digital video of X-ray images in three phases. The first phase is the start-up phase where the system 100 acquires image data for a brief time while X-ray shooting is anticipated. The image data in the first phase produces a series of blank or black leader images. The leader images may represent image data acquired by the image sensor 112 before the X-ray source 102 starts emitting X-rays. The second phase is the X-ray exposure phase where the system 100 acquires X-ray image data for the image sequence. The third phase is the termination phase where a series of blank or black trailer images are acquired after the X-ray exposure has terminated. The trailer images may represent image data acquired by the image sensor 112 after the X-ray source stops emitting the X-rays. The resulting image sequence may have a duration of approximately 15 seconds with 2 seconds of meaningful X-ray image data.

The processing system 118 can automatically edit the sequence of images captured by the image sensor 112 to generate the digital video of X-ray images. The sequence of images captured by the image sensor 112 during a video capture session may include approximately 2 seconds of X-ray images surrounded by the blank or black leader and trailer images. For example, the sequence of images may include approximately 5 seconds of leader images followed by 2 seconds of X-ray images and 10 seconds of trailer images. The processing system 118 may automatically edit the sequence of images to eliminate the leader images and trailer images, leaving only the sequence of X-ray images in the digital video. The processing system 118 may eliminate the leader images and trailer images by, for example, detecting black images and removing the black images from the sequence of images. The processing system 118 may edit and present the digital video within approximately 10 seconds of receiving the digital signals representing the sequence of images from the image sensor 112. The processing system 118 may present the digital video in a closed loop, e.g., in forward and reverse playback, so that the series of images appear to represent a continuous motion of a moving object in a bidirectional orientation.

The processing system 118 may display a user interface for presenting a digital still X-ray image or a digital video of X-ray images. The user interface can include user interface elements, such as selectable buttons, scroll bars, and data fields, that allow a user to manipulate, adjust, and annotate the image data. For example, the user can provide input to adjust the playback speed, adjust brightness and contrast, adjust the zoom level, grab, measure an object, or enter text in an X-ray image or video.

Figure 2:
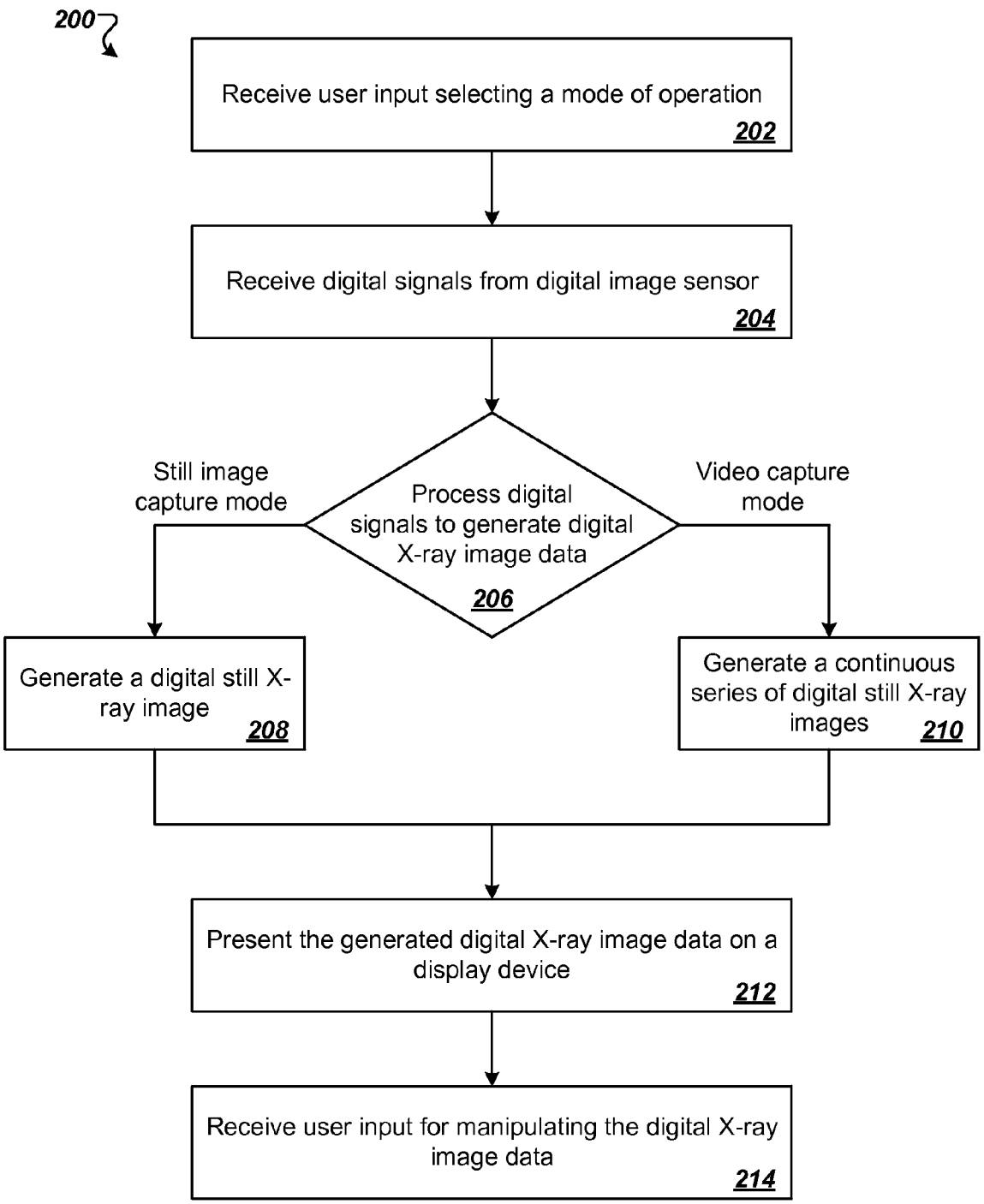
FIG. 2 is a flowchart of an example of a process for generating and presenting digital X-ray image data.

FIG. 2 is a flowchart of an example of a process 200 performed by a processing system, such as the processing system 118 of FIG. 1, for generating digital X-ray image data and presenting the digital X-ray image data. At 202, the processing system receives user input that selects a mode of operation from between a still image capture mode and a video capture mode.

At 204, the processing system receives digital signals from a digital image sensor, such as the digital image sensor 112 of FIG. 1. When the selected mode of operation is the still image capture mode, the processing system may receive a set of digital signals representing a single digital still X-ray image from the digital image sensor. When the selected mode of operation is the video capture mode, the processing system may receive multiple sets of digital signals representing a continuous series of digital still X-ray images.

For example, in the video capture mode, the processing system may receive a first set of digital signals that are generated by the image sensor before the X-ray source starts emitting the X-rays. The first set of digital signals may represent the leader images of the image sequence. While the X-ray source is emitting the X-rays, the processing system may receive a second set of digital signals. The second set of digital signals may represent the X-ray images of the image sequence. After the X-ray source stops emitting the X-rays, the processing system may receive a third set of digital signals. The third set of digital signals may represent the trailer images of the image sequence.

At 206, the processing system processes the digital signals to generate digital X-ray image data in accordance with the selected mode of operation. When the selected mode of operation is the still image capture mode, the processing system generates a digital still X-ray image at 208. The digital still X-ray image may have an image resolution up to 6000× 4000 pixels, e.g., in a range of 5000×3000 pixels to 6000× 4000 pixels, or a larger array of pixels.

When the selected mode of operation is the video capture mode, the processing system generates a continuous series of digital still X-ray images at 210. The continuous series of digital still X-ray images may have a frame rate up to 30 frames per second, e.g., in a range of 24 frames per second to 30 frames per second. The continuous series of digital still X-ray images may have a duration up to 2 seconds, e.g., in a range of 1 second to 2 seconds. The continuous series of digital still X-ray images may include digital still X-ray images having image resolutions up to 1920×1080 pixels, e.g., in a range of 800×600 pixels to 1920×1080 pixels.

To generate the continuous series of digital still X-ray images, the processing system may generate a first set of digital X-ray image data from the first set of digital signals, a second set of digital X-ray image data from the second set of digital signals, and a third set of digital X-ray image data from the third set of digital signals. The first set of digital X-ray image data may include the leader images, the second set of digital X-ray image data may include the X-ray images, and the third set of digital X-ray image data may include the trailer images. The processing system may generate the continuous series of digital still X-ray images from the first set of digital X-ray image data, the second set of digital X-ray image data, and the third set of digital X-ray image data. The processing system may determine that the first set of digital X-ray image data and the third set of digital X-ray image data includes only blank images, and remove the first set of digital X-ray image data and the third set of digital X-ray image data from the continuous series of digital still X-ray images.

At 212, the processing system presents the generated digital X-ray image data on a display device, such as the display device 120 of FIG. 1. The processing system may present the digital X-ray image data on the display device within approximately 10 seconds of receiving the digital signals from the digital image sensor. If the generated digital X-ray image data is a continuous series of digital still X-ray images, the processing system may present the continuous series of digital still X-ray images, e.g., approximately 1 to 2 seconds of the digital video of the X-ray data, in a forward direction followed by a reverse direction so that an object in the continuous series of digital still X-ray images moves continuously in one direction followed by the other direction.

At 214, the processing system may receive user input for manipulating the digital X-ray image data. For example, the processing system may receive user input to slow playback speed, adjust brightness, adjust contrast, zoom, grab, measure, or annotate the digital X-ray image data.

Implementations of the subject matter and the operations described in this specification can be implemented in digital electronic circuitry, or in computer software, firmware, or hardware, including the structures disclosed in this specification and their structural equivalents, or in combinations of one or more of them. Implementations of the subject matter described in this specification can be implemented as one or more computer programs, i.e., one or more modules of computer program instructions, encoded on computer storage medium for execution by, or to control the operation of, data processing apparatus. Alternatively or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can be, or be included in, one or more separate physical components or media (e.g., multiple CDs, disks, or other storage devices).

The operations described in this specification can be implemented as operations performed by a data processing apparatus on data stored on one or more computer-readable storage devices or received from other sources. The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application-specific integrated circuit). The apparatus can include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, implementations of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

Figure 3:
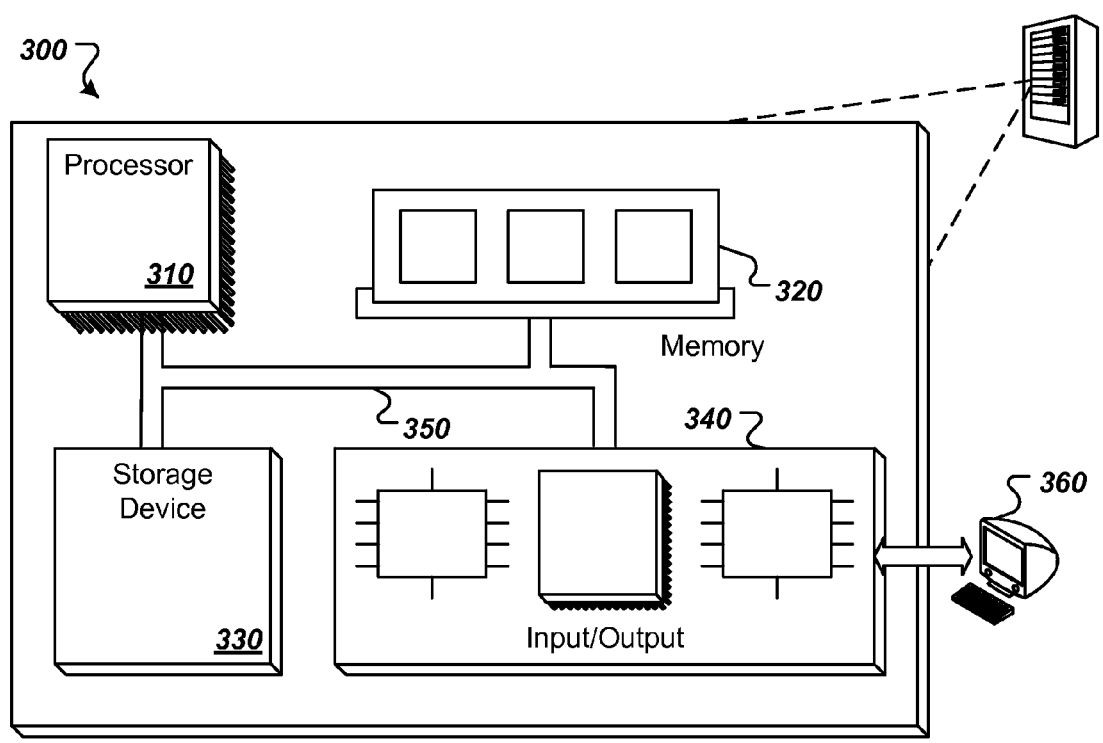
FIG. 3 is a block diagram of a programmable processing system.

An example of one such type of computer is shown in FIG. 3, which shows a block diagram of a programmable processing system (system). The system 300 that can be utilized to implement the systems and methods described herein. The architecture of the system 300 can, for example, be used to implement a computer client, a computer server, or some other computer device.

The system 300 includes a processor 310, a memory 320, a storage device 330, and an input/output device 340. Each of the components 310, 320, 330, and 340 can, for example, be interconnected using a system bus 350. The processor 310 is capable of processing instructions for execution within the system 300. In one implementation, the processor 310 is a single-threaded processor. In another implementation, the processor 310 is a multi-threaded processor. The processor 310 is capable of processing instructions stored in the memory 320 or on the storage device 330.

The memory 320 stores information within the system 300. In one implementation, the memory 320 is a computer-readable medium. In one implementation, the memory 320 is a volatile memory unit. In another implementation, the memory 320 is a non-volatile memory unit.

The storage device 330 is capable of providing mass storage for the system 300. In one implementation, the storage device 330 is a computer-readable medium. In various different implementations, the storage device 330 can, for example, include a hard disk device, an optical disk device, or some other large capacity storage device.

The input/output device 340 provides input/output operations for the system 300. In one implementation, the input/output device 340 can include one or more of a network interface device, e.g., an Ethernet card, a serial communication device, e.g., and RS-232 port, and/or a wireless interface device, e.g., an 802.11 card. In another implementation, the input/output device can include driver devices configured to receive input data and send output data to other input/output devices, e.g., keyboard, printer, and display devices 360.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can be implemented in combination in a single implementation. Conversely, various features that are described in the context of a single implementation can be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

Thus, particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

What is claimed is:

1. A system comprising:
   (a) a conventional, film-based X-ray machine including:
      (i) an X-ray source that emits X-rays, and
      (ii) a bracket assembly configured to hold X-ray film;
   (b) a digital imaging assembly configured to be mounted on the bracket assembly of the conventional, film-based X-ray machine, the digital imaging assembly including:
      (i) a scintillation screen that converts X-ray photons into visible light photons, and
      (ii) a digital image sensor that converts the visible light photons into digital signals; and
   (c) one or more processors coupled with the digital image sensor, the one or more processors configured to perform operations including:
      (i) receive user input that selects a mode of operation from between a still image capture mode and a video capture mode,
      (ii) receive the digital signals from the digital image sensor,
      (iii) process the digital signals to generate digital X-ray image data in accordance with the selected mode of operation, and
      (iv) present the generated digital X-ray image data on a display device.

2. The system of claim 1, wherein the digital imaging assembly includes a lens that focuses the visible light photons from the scintillation screen onto the digital image sensor.

3. The system of claim 1, wherein the one or more processors is configured to perform an operation to generate a digital still X-ray image when the selected mode of operation is the still image capture mode.

4. The system of claim 3, wherein the one or more processors is configured to perform an operation to generate the digital still X-ray image with an image resolution in a range of 5000×3000 pixels to 6000×4000 pixels.

5. The system of claim 1, wherein the one or more processors is configured to perform an operation to generate a continuous series of digital still X-ray images when the selected mode of operation is the video capture mode.

6. The system of claim 5, wherein the one or more processors is configured to perform an operation to generate the continuous series of digital still X-ray images with a frame rate in a range of 24 frames per second to 30 frames per second.

7. The system of claim 5, wherein the one or more processors is configured to perform an operation to generate the continuous series of digital still X-ray images with a duration in a range of 1 second to 2 seconds.

8. The system of claim 5, wherein the one or more processors is configured to perform an operation to generate the continuous series of digital still X-ray images with each of the digital still X-ray images having an image resolution in a range of 800×600 pixels to 1920×1080 pixels.

9. The system of claim 5, wherein the one or more processors is configured to perform operations including:
   receive a first set of digital signals that are generated by the digital image sensor before the X-ray source starts emitting the X-rays;
   receive a second set of digital signals that are generated by the digital image sensor while the X-ray source is emitting the X-rays; and
   receive a third set of digital signals that are generated by the digital image sensor after the X-ray source stops emitting the X-rays.

10. The system of claim 9, wherein the one or more processors is configured to perform operations including:
   generate a first set of digital X-ray image data from the first set of digital signals, a second set of digital X-ray image data from the second set of digital signals, and a third set of digital X-ray image data from the third set of digital signals;
   generate the continuous series of digital still X-ray images from the first set of digital X-ray image data, the second set of digital X-ray image data, and the third set of digital X-ray image data;
   determine that the first set of digital X-ray image data and the third set of digital X-ray image data includes only blank images;

remove the first set of digital X-ray image data and the third set of digital X-ray image data from the continuous series of digital still X-ray images; and present the continuous series of digital still X-ray images in a forward direction and in a reverse direction.

11. The system of claim 1, wherein the one or more processors is configured to perform an operation to present the generated digital X-ray image data on the display device within 10 seconds of receiving the digital signals from the digital image sensor.

12. The system of claim 1, wherein the one or more processors is configured to perform an operation to receive user input to slow playback speed, adjust brightness, adjust contrast, zoom, grab, measure, or manipulate the digital X-ray image data.

13. The system of claim 1, wherein the digital image sensor comprises at least one of a charge-coupled device (CCD) imaging array or a complementary metal-oxide-semiconductor (CMOS) imaging array.

14. The system of claim 1, wherein the conventional, film-based X-ray machine includes a controller that causes the X-ray source to emit the X-rays in response to user input received by the controller.

15. The system of claim 14, wherein the one or more processors is coupled with the controller of the conventional, film-based X-ray machine, the one or more processors configured to perform an operation to transmit a signal to the controller to cause the X-ray source to emit the X-rays.

16. A method comprising:
obtaining a conventional, film-based X-ray machine, the X-ray machine including:
an X-ray source that emits X-rays, and
a bracket assembly configured to hold X-ray film;
retrofitting the conventional, film-based X-ray machine with a digital imaging system configured to capture digital still X-ray images and digital videos of a series of X-ray images, the digital imaging system comprising:
a digital imaging assembly configured to be mounted on the bracket assembly of the conventional, film-based X-ray machine, the digital imaging assembly including:
(i) a scintillation screen that converts X-ray photons into visible light photons, and
(ii) a digital image sensor that converts the visible light photons into digital signals; and
one or more processors coupled with the digital image sensor, the one or more processors configured to perform operations including:
(i) receive user input that selects a mode of operation from between a still image capture mode and a video capture mode,
(ii) receive the digital signals from the digital image sensor,
(iii) process the digital signals to generate digital X-ray image data in accordance with the selected mode of operation, and
(iv) present the generated digital X-ray image data on a display device.

17. The method of claim 16, further comprising:
using the retrofitted conventional, film-based X-ray machine to capture digital still X-ray images when the selected mode of operation is the still image capture mode.

18. The method of claim 16, further comprising:
using the retrofitted conventional, film-based X-ray machine to capture digital videos of a series of X-ray images when the selected mode of operation is the video capture mode.

19. The method of claim 16, further comprising:
using the retrofitted conventional, film-based X-ray machine to manipulate the digital X-ray image data.

20. The method of claim 16, further comprising:
using the digital imaging system to cause the conventional, film-based X-ray machine to emit the X-rays.

* * * * *